United States Patent [19]
Chung

[11] Patent Number: 5,683,988
[45] Date of Patent: Nov. 4, 1997

[54] ANTI-SENSE OLIGODEOXYNUCLEOTIDE TO FIBROGENIC CYTOKINE TGF-β AND USE THEREOF

[75] Inventor: Hun-Taeg Chung, Iri, Rep. of Korea

[73] Assignee: Il-Yang Pharm. Co., Ltd., Seoul, Rep. of Korea

[21] Appl. No.: 580,242

[22] Filed: Dec. 28, 1995

Related U.S. Application Data

[63] Continuation-in-part of Ser. No. 132,259, Oct. 6, 1993, abandoned.

[30] Foreign Application Priority Data

Jun. 15, 1993 [KR] Rep. of Korea ............. 93.10883

[51] Int. Cl.$^6$ .................. A61K 48/00; C07H 21/04
[52] U.S. Cl. ................. 514/44; 536/24.5; 536/25.3
[58] Field of Search ................. 514/44; 536/24.5, 536/25.3

[56] References Cited

FOREIGN PATENT DOCUMENTS

WO 92/17206  10/1992  WIPO.

OTHER PUBLICATIONS

"Immunohistochemical Localization of Growth Factors in Fetal Wound Healing", D.J. Whitby et al., Dev. Biolo. 147: pp. 207–215, 1991.
"Control of Scarring in Adult Wounds By Neutralizing Antibody to Transforming Growth Factor", M. Shah et al., Lancet 339, pp. 213–214, 1992.
"Transforming Growth Factor–β in Disease: The Dark Side of Tissue Repair", W.A. Border et al., J. Clin. Invest. 90: pp. 1–7, 1992.
"IFN–π Induces the Expression of the Genes For MHC Class II I=Aβ and Tumor Necrosis Factor Through 1 Protein Kinase C–Independent Pathway", Antonio Celada et al., Journal of Immunology 146, pp. 114–120, 1991.
"Tumor Necrosis Factor–α–Dependent Production of Reactive Nitrogen Intermediates Mediates IFN–π Plus IL–2–Induced Murine Macrophage Tumoricidal Activity", G.W. Cox et al., Journal of Immunology 149, pp. 3290–3296, 1992.
"Release of Reactive Nitrogen Intermediates and Reactive Oxygen Intermediates from Mouse Peritoneal Macrophages", Aihao Ding et al, Journal of Immunology 141, pp. 2407–2412, 1988.

Primary Examiner—Bruce R. Campell
Attorney, Agent, or Firm—Lowe, Price, LeBlanc & Becker

[57] ABSTRACT

The present invention relates to an anti-sense oligodeoxynucleotide to mRNA for one of major fibrogenic cytokines, TGF-β, which is secreted in large quantities in wound portion and then stimulates the fibrinoid degeneration of the tissue. The anti-sense oligodeoxynucleotide according to the present invention is complementarily bound to mRNA of TGF-β to inhibit the genetic expression thereof and thus can inhibit the scarring due to the production of fibrogenic cytokines and the fibrinoid degeneration at the wound portion to treat the wound portion so as to have an appearance substantially identical to the normal tissue. Accordingly, the present invention also relates to the use of anti-sense oligodeoxynucleotide to TGF-β as a scarring inhibitor.

9 Claims, 3 Drawing Sheets

M : DNA size marker

← : Product band

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 19 base pairs
( B ) TYPE: nucleic acid (C) STRANDEDNESS: single
(D) TOPOLOGY: linear (ii) MOLECULE TYPE: DNA (genomic)

(iv) ANTI-SENSE: YES (xi) SEQUENCE DESCRIPTION: SEQ ID NO:1:

CCGAGAGCGC GAACAGGGC  19

(2) INFORMATION FOR SEQ ID NO:2:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(iv) ANTI-SENSE: YES (xi) SEQUENCE DESCRIPTION: SEQ ID NO:2:

GGTGTGGTGG GGAGG  15

(2) INFORMATION FOR SEQ ID NO:3:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(iv) ANTI-SENSE: YES (xi) SEQUENCE DESCRIPTION: SEQ ID NO:3:

GGCTGGGGGT CACCC  15

(2) INFORMATION FOR SEQ ID NO:4:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(iv) ANTI-SENSE: YES (xi) SEQUENCE DESCRIPTION: SEQ ID NO:4:

AGAGAGATCC GTCTC  15

(2) INFORMATION FOR SEQ ID NO:5:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(iv) ANTI-SENSE: YES (xi) SEQUENCE DESCRIPTION: SEQ ID NO:5:

CCCGGAGGGC GGCAT  15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:6:

GGCAAAAGGT AGGAG      15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:7:

GAAAGCTGAG GCTCC      15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:8:

GAGAAGGGCG CAGTG      15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:9:

GTGGAGGGA GGCTT      15

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:10:

TGTCTCAGTA TCCCA                                                                                   15

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GGGAAATTGA GGGCTTTCGC                                                                              20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CTGAAGCAAT AGTTGGTGTC                                                                              20

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAATTTGGGC CCAAA                                                                                   15

ANTI-SENSE OLIGODEOXYNUCLEOTIDE TO FIBROGENIC CYTOKINE TGF-β AND USE THEREOF

CROSS-REFERENCE TO RELATED APPLICATION

This application is a continuation-in-part of U.S. patent application Ser. No. 08/132,259 filed Oct. 6, 1993, abandoned.

BACKGROUND OF THE INVENTION

1. Field of the Invention

The present invention relates to a novel anti-sense oligodeoxynucleotide to fibrogenic cytokines. Particularly, the present invention relates to a novel anti-sense oligodeoxynucleotide which can inhibit the gene expression of fibrogenic cytokine TGF-β secreted in wound portion in a large amount to prevent scar formation. The present invention also relates to the use of anti-sense oligodeoxynucleotide to fibrogenic cytokine TGF-β as a scarring inhibitor.

2. Background Art

Immunological response, inflammatory response and tissue repair response display a function for prevention of host organisms from dangerous surrounding environments. However, if such responses do not smoothly occur or excessively occur, such responses may make a damage to host organisms but cannot prevent host organisms. As one example of biological processes involving such responses, wound healing process results in formation of scar, as one of tissue repair response to trauma, surgical operation, burns and the like, and scar thus formed may frequently be constricted to inhibit the growth of tissue or to lead to a functional disorder or to deteriorate external appearance of host.

Wound healing process is a very elaborate tissue response in which acute and chronic inflammation, cell migration, vascularization, accumulation of extra cellular matrix (ECM), etc. successively occur. When wound occurs, blood vessel surrounding the wound tissue is injured to cause focal bleeding, and then fibrinogen present in blood clot forms fibrin gel into which plasma proteins such as fibronectin are introduced. Further, other cells such as inflammatory cell, fibroblast, vascularization cell and the like are introduced into such gel to liquify the gel while fibronectin accumulates ECM components such as collagen, proteoglycan, etc. in the tissue surrounding wound. As a result of this process, fibrin matrix originally present in the tissue is replaced with granulation tissue on which scar is formed, as time goes by, and ECM accumulation and at the same time keratinocyte migration result in formation of epithelial membrane which can prevent fluid loss and bacterial invasion. Such procedures involved in this wound healing process can be accomplished by interaction of immunological cell, inflammatory cell and mesenchymal cell of impaired tissue with various cytokines such as transforming growth factor-β (TGF-β), platelet-derived growth factor (PDGF), fibroblast growth factor (FGF) and fibroblast activating factor (FAF), and ECMs such as collagen, fibronectin, tenascin and proteoglycan.

It has been found that among various cytokines which can promote fibroblast proliferation and increase ECM accumulation in wound tissue, especially TGF-β and PDGF play the most important role. It has also been disclosed that TGF-β significantly increases fibroblast proliferation and further expression of gene for ECMs such as collagen and fibronectin and that PDGF has a little effect on collagen synthesis but greatly promotes the proliferation of fibroblast.

In addition, according to the recent study it has been reported that in the case of fetal wounds the wound healing process does not result in scarring and causes a little inflammatory response and cytokine secretion in comparison to those in adult wounds [see, Whitby, D. J. and M. W. J. Ferguson, 1991, Immunohistochemical localization of growth factors in fetal wound healing, Dev. Biol. 147: 207–215]. In this reference, however, it is also described that upon the injection of TGF-β into the tissue surrounding wound, scar formation may be caused even in the case of fetal wounds and further glomerulonephritis may be induced.

According as the relation of scar with cytokines is identified, it has been proposed that the control of cytokines may inhibit the formation of scar. For instance, Shah M., et al. could observe that on the basis of the fact that TGF-β is physiologically secreted in an excessive amount during the wound healing process, when a wound is artificially formed on rat and then neutralizing antibody(NA) for TGF-β is injected around wound, the wound portion treated with neutralizing antibody does not show any change in tensile strength of the tissue and further is recovered more nearly to a normal skin tissue appearance, in comparison with the wound of the control group which is not treated with said antibody [see, Shah M., Foreman D M., Ferguson M W J., 1992, Control of scarring in adult wounds by neutralizing antibody to transforming growth factor β, Lancet 339: 213–214]. In addition, in this experiment it has also been identified that the wound treated with neutralizing antibody is cured without any scarring whereas the wound portion of the control group, which is not treated with neutralizing antibody, shows more inflammatory cells and accumulates the larger amount of ECMs such as collagen or fibronectin, in comparison with the wound treated with neutralizing antibody. However, such neutralizing antibody has a difficulty in practical application because it is very expensive and is too unstable for storage.

Additionally, Border W A., et al. have identified that as a result of administration of decorin, which is one of proteoglycan ECMs and can be bound to TGF-β receptor and therefore can act as an inhibitor to TGF-β, to glomerulonephritis animal model, decorin can inhibit fibrinoid degeneration to prevent glomerulonephritis [see, Border W A, Rouslahti E, 1992, Transforming growth factor-β in disease: The dark sude of tissue repair, J. Clin. Invest. 90: 1–7]. However, protein agents such as decorin are difficult to permeate into cells because of their macromolecular structures, and therefore, can be administered only through the oral route. Accordingly, they have a difficulty in obtaining an effective level of the drug at the desired wound site.

As the most traditional and general method, in addition to the above mentioned methods, the use of synthetic medicinal agents such as steroids has been practically applied. However, such medicinal agents have no direct inhibiting effects on the scar formation and further have a disadvantage due to typical side effects of steroidal agents and the like.

SUMMARY OF THE INVENTION

On the basis of the above mentioned prior art, the present inventor has extensively studied to find out the means which can prevent the formation of scar at the wound portion more fundamentally by inhibiting the production of fibrogenic cytokines themselves rather than inhibiting or blocking the action already produced fibrogenic cytokines. As a result, the present inventor has identified that the use of a specific anti-sense oligodeoxynucleotide to mRNA for fibrogenic cytokines, particularly TGF-β, can provide the desired effect and then completed the present invention.

Therefore, it is an object of the present invention to provide a novel anti-sense oligodeoxynucleotide to mRNA for fibrogenic cytokine TGF-β which is secreted in large quantities at wound portion and then stimulates the fibrinoid degeneration of the tissue.

It is a further object of this invention to provide a composition for scarring inhibition which comprises an amount of anti-sense oligodeoxynucleotide to TGF-β mRNA effective to inhibit the genetic expression of TGF-β and thus to inhibit the scarring in wound portion.

It is a further object of this invention to provide a use of anti-sense oligodeoxynucleotide as a scarring inhibitor.

It is a further object of this invention to provide a method of producing the novel anti-sense oligodeoxynucleotide to TGF-β in large quantities.

The foregoing has outlined some of the more pertinent objects of the present invention. These objects should be construed to be merely illustrative of some of the more pertinent features and applications of the invention. Many other beneficial results can be obtained by applying the disclosed in a different manner or modifying the invention within the scope of the disclosure. Accordingly, other objects and a more thorough understanding of the invention may be had by referring to the summary of the invention and the detailed description describing the preferred embodiment in addition to the scope of the invention defined by the claims taken in conjunction with the accompanying drawings.

BRIEF DESCRIPTION OF THE DRAWINGS

For a thorough understanding of the nature and objects of the invention, reference should be had to the following detailed description taken in connection with the accompanying drawings in which.

DESCRIPTION OF THE INVENTION

Figure 1:
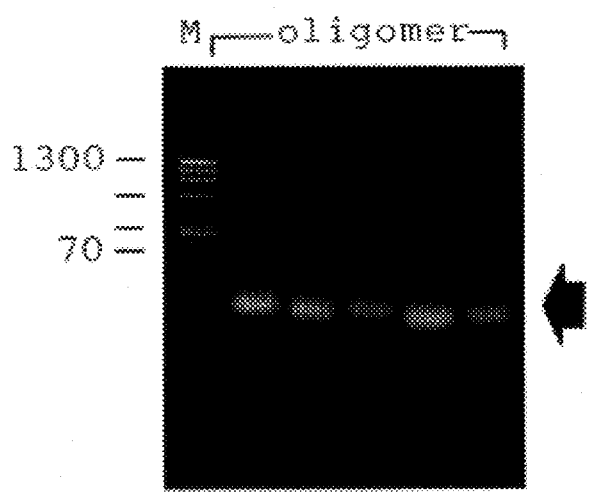
FIG. 1 is an electrophoretic diagram of anti-sense oligodeoxynucleotide to TGF-β as prepared in Example 1.

In one aspect, the present invention relates to a novel anti-sense oligodeoxynucleotide to fibrogenic cytokines. Particularly, the present invention relates to a novel anti-sense oligodeoxynucleotide which can be complementarily bound to mRNA of TGF-β, as typical one of fibrogenic cytokines, to inhibit the genetic expression of TGF-β and thus can substantially or completely prevent the scarring at the wound portion of animal.

When the anti-sense oligodeoxynucleotide to mRNA for TGF-β according to the present invention is applied to the peripheral tissue of wound, it is complementarily bound to TGF-β mRNA to form a hybrid and thus to inhibit the genetic expression of TGF-β, whereby the production of TGF-β at the periphery of wound can be inhibited to prevent the formation of scar.

The anti-sense oligodeoxynucleotide according to the present invention is to mRNA for one of major fibrogenic cytokines, i.e. transforming growth factor-β (TGF-β) which induces most strongly the proliferation of fibroblast and the production of connective tissue.

Typical examples of anti-sense oligodeoxynucleotides according to the present invention are illustrated hereinafter.

5'-CCGAGAGCGCGAACAGGGC-3' (SEQ ID NO:1);
5'-GGTGTGGTGGGGAGG-3' (SEQ ID NO:2);
5'-GGCTGGGGGTCACCC-3' (SEQ ID NO:3);
5'-AGAGAGATCCGTCTC-3' (SEQ ID NO:4);
5'-CCCGGAGGGCGGCAT-3' (seq ID NO:5);
5'-GGCAAAAGGTAGGAG-3' (SEQ ID NO:6);
5'-GAAAGCTGAGGCTCC-3' (SEQ ID NO:7);
5'-GAGAAGGGCGCAGTG-3' (SEQ ID NO:8);
5'-GTGGAGGGGAGGCTT-3' (SEQ ID NO:9); and
5'-TGTCTCAGTATCCCA-3' (SEQ ID NO:10).

Although the anti-sense oligodeoxynucleotide according to the present invention can be prepared by conventional chemical nucleotide synthetic methods, for the convenience of preparation it is preferably synthesized by means of a computerized automatic DNA synthesizer. During this synthetic procedure, the total base is modified by substitution of oxygen atom in phosphate group with sulfur atom to prevent the base from cleavage with nuclease. For this purpose, for example, tetraethylthiuram disulfide can be preferably used. However, since the modification of phosphate group has substantially no influence on the pharmacological effect when anti-sense oligodeoxynucleotide is applied to the skin, the base may be synthesized and used in the unmodified, i.e. unprotected, form. However, since the unmodified sequence is very sensitive to endonuclease naturally occurring in tissue, the anti-sense oligodeoxynucleotide modified by sulfurization, i.e. S thiolated anti-sense oligodeoxynucleotides, which is relatively high resistant to endonuclease is preferably used for longer duration of the therapeutic effect at the desired tissue. Then, the synthesized anti-sense oligodeoxynucleotide is conjugated with linkers at both ends and is introduced into a suitable vector plasmid to construct the recombinant plasmid with which the host bacteria is transformed. The obtained transformant is incubated under suitable conditions to express anti-sense oligodeoxynucleotide in a large amount, which is then digested with restriction enzymes to separate and obtain only the desired anti-sense oligodeoxynucleotide in a pure state.

Plasmid which can be preferably used in the above procedures is, for example, pSPT18, pSPT19, pBluescript, pGEM-3, etc., with plasmid pBluescript being particularly preferable. In transforming with a recombinant plasmid comprising such plasmid and anti-sense oligodeoxynucleotide, the preferable host organism is E. coli HB101.

The anti-sense oligodeoxynucleotide thus prepared according to the above method can inhibit the production of fibrogenic cytokine TGF-β, which is known as being secreted in large quantities at the periphery of wound, as mentioned above and therefore can be used as an inhibitor to scar formation. Thus, the present invention further relates to use of a novel anti-sense oligodeoxynucleotide defined above as an inhibitor to scarring.

When using the anti-sense oligodeoxynucleotide to TGF-β mRNA as the scarring inhibitor, it can be used alone or, if required, in an admixture with anti-sense oligodeoxynucleotides to one or more other fibrogenic cytokines. For example, the use of a mixture of anti-sense oligodeoxynucleotide to TGF-β according to the present invention and anti-sense oligodeoxynucleotide to TNF- can provide more rapid wound healing effect.

The anti-sense oligodeoxynucleotide according to the present invention can be formulated into a pharmaceutically acceptable preparation, for example, injections, sprays, ointments, creams and the like, with pharmaceutically acceptable conventional carriers and then administered either systemically or locally on the wound lesion. The pharmaceutically acceptable conventional carriers which can be used for this purpose may include distilled water for injection, phosphate buffer, physiological saline, etc. in the case of injections; ethanol, propylene glycol, glycerin, propellant, etc. in the case of sprays; and polyethylene glycol, liquid paraffin, carnauba wax, etc. in the case of formulation for topical use such as ointments and creams.

Although the dose of anti-sense oligodeoxynucleotide to TGF-β mRNA according to the present invention can be varied with extent, severity and the like of wound lesion and condition of the subject for application, the anti-sense oligodeoxynucleotide is generally used in an amount of approximately 10 μM for each time, 3 to 5 times per day.

The anti-sense oligodeoxynucleotide according to the present invention acts only on the genetic expression procedure for TGF-β involved in scar formation due to the fibrinoid degeneration of tissues and does not cause special side effects and toxicity. Moreover, since it is used in an extremely low amount of about 10 μM, the anti-sense oligodeoxynucleotide according to the present invention has substantially no side effects.

The present invention will be more specifically illustrated by the following examples but it should be understood that the present invention is not limited to these examples in any manner.

EXAMPLE 1

Synthesis of anti-sense oligodeoxynucleotide 5'-CCGAGAGCGCGAACAGGGC-3' (SEQ ID NO:1) to mRNA for TGF-β

GENE ASSEMBLER SPECIAL (Pharmacia, LKB), as an automatized DNA synthesizer, which is equipped with bottles containing acetonitrile for washing cartridge, dichloroacetic acid for removing base-protecting groups and monodisperse plastic bead for removing water, respectively, and is programmed so that base C(cytosine) is used as a starting material and the desired amounts of bases A(adenine), G(guanine) and C(cytosine) are introduced in the desired order, was operated at the room temperature for 2.5 hours to synthesize the desired anti-sense oligodeoxynucleotide 5'-CCGAGAGCGCGAACAGGGC-3 (SEQ ID NO:1) to TGF-β.

The linker sequences GGGCC which provide the cutting site for Apa I were bound to both ends of anti-sense oligodeoxynucleotide thus prepared above. The obtained nucleotide sequence was introduced into the Apa I-cutting site of plasmid pBluescript to obtain the recombinant expression plasmid. The recombinant plasmid thus obtained was introduced into the host bacterial strain E. coli HB101 to yield the transformant. The transformed E. coli HB101 was incubated in LB medium at 37° C. for about 16 hours to express the desired anti-sense oligodeoxynucleotide. The isolated plasmid was digested with restriction enzyme Apa I to obtain a pure anti-sense oligodeoxynucleotide having the desired sequence. The absorbance of the resulting product was measured at 260 nm using a spectrophotometer. The yield of the desired product was 92%. According to base sequence analysis and electrophoresis (FIG. 1) of the produced anti-sense oligodeoxynucleotide, it could be identified that the desired title anti-sense sequence was obtained by the above procedure.

EXAMPLE 2

According to the substantially same procedure as Example 1, the following nine kinds of anti-sense oligodeoxynucleotide to TGF-β mRNA were synthesized:

1. 5'-GGTGTGGTGGGGAGG-3' (SEQ ID NO:2);
2. 5'-GGCTGGGGGTCACCC-3' (SEQ ID NO:3);
3. 5'-AGAGAGATCCGTCTC-3' (SEQ ID NO:4);
4. 5'-CCCGGAGGGCGGCAT-3' (seq ID NO:5);
5. 5'-GGCAAAAGGTAGGAG-3' (SEQ ID NO:6);
6. 5'-GAAAGCTGAGGCTCC-3' (SEQ ID NO:7);
7. 5'-GAGAAGGGCGCAGTG-3' (SEQ ID NO:8);
8. 5'-GTGGAGGGGAGGCTT-3' (SEQ ID NO:9); and
9. 5'-TGTCTCAGTATCCCA-3' (SEQ ID NO:10).

After the respective anti-sense oligodeoxynucleotide sequence is synthesized, it was sulfurized by using tetraethylthiuram disulfide (TETD) in an amount of 6 ml per each base in 25 μmol scale synthesis to obtain the S thiolated anti-sense oligodeoxynucleotide, which was then purified by means of reverse column [A solvent: 100% 0.1M triethylamine acetate(TEAA), B solvent: 50% 0.1M TEAA+50% acetonitrile; A solvent is replaced by B solvent with linear gradient during 4 minutes] and treated with 0.6 ml of 80% acetic acid per 1 mg of the synthesized oligomer to remove the trityl group. The resulting product was precipitated with ethanol and lyophilized to obtain the desired S thiolated anti-sense oligodeoxynucleotide corresponding to the above SEQ ID NOS. 2 to 10 in the powder form.

EXAMPLE 3

Effect of anti-sense oligodeoxynucleotide SEQ ID NO:1 to TGF-β on the genetic expression for TGF-β

Wound was experimentally induced in animal to which anti-sense oligodeoxynucleotide to TGF-β as a typical fibrogenic cytokine was administered. Then, the effect of the administered anti-sense oligodeoxynucleotide on the expression of TGF-β in the test group was determined in comparison with the control group to which no anti-sense oligodeoxynucleotide is administered.

1) After Balb/C mouse was anesthetized with ether, hair on the back portion of mouse was completely removed by using a hair cutter and thioglycolic acid. The back portion from the center to the limbs was cut down on four positions at the same intervals up to just above the muscle which were not sutured to induce spontaneous healing. At that time, one group of mouse was treated with 50 μM of anti-sense oligodeoxynucleotide 5'-CCGAGAGCGCGAACAGGGC-3' (SEQ ID NO:1) to TGF-β as prepared in Example 1 and the other group of mouse was used as the control group. In each group, the expression of TGF-β was measured as the trauma healing period has passed.

Just after wound induction and 1, 2, 3, 5 and 10 weeks after wound induction the tissue of wound portion was separated from each group of mouse to collect the cells. The collected cells were washed with phosphate buffered saline (PBS) which does not contain $Ca^{2+}$, $Mg^{2+}$ and RNase, and then were introduced into NP-40 lysis buffer [0.5% NP-40, 10 mM Tris-Cl(pH8.0), 100 mM Nacl, 3 mM MgCl$_2$, 1000 U/ml RNAsin (Promega)] and centrifuged with 12000 rpm for 2 minutes to remove cellular nucleus. The supernatant can be then separated and used directly as RNA source.

According to the other method, 1×10$^8$ cells were dissolved in 4 ml of GIT buffer [4M guanidine thiocyanate, 50 mM Tris-Cl(pH8.0), 10 mM EDTA (ethylenediaminetetraacetate), 0.5% sodium lauryl sarcosine, 0.1M mercaptoethanol] and then loaded on 7 ml of 5.7M CsCl buffer and centrifuged with 80000 rpm for about 2 hours at 25° C. Thus, the total RNAs which were attached to the bottom and wall of test tube were obtained. To separate poly(A)$^+$ mRNA in a pure state, an appropriate amount of oligotex-dT was added to the obtained RNAs with using TE buffer (Tris-HCl 10 mmol/L, EDTA 1 mmol/L, pH8.0) as the eluant. The mixture was heated for 5 minutes at 65° C., rapidly cooled with ice and then incubated with 1/10 volume of 5M NaCl for 5 to 10 minutes at 37° C. Thereafter, the culture solution was centrifuged with 15000 rpm for 5 to 10 minutes. After removing the supernatant, the residue was mixed with sterilized distilled water, heated again at 65° C. for 5 minutes and then centrifuged with 15000 rpm for 5 to 10 minutes. The resulting product was precipitated with ethanol and then dissolved in diethylpyrrocarbonate(DEPC)-dH$_2$O to obtain the desired mRNa mRNA thus prepared above was denatured at 65° to 75° C. for 10 minutes. 1 to 2 μg of the denatured mRNA was added together with 0.5 μg of oligo(dT)$_{12-18}$ (Pharmacia), 1×Taq polymerase buffer (50 mM Tris-Cl, pH8.3, 3 mM MgCl$_2$, 250 μg/ml BSA), 1.25 mM dNTP, 2.5 mM MgCl$_2$, 20 units of RNAsin(BRL) and 100 units of murine reverse transcriptase(BRL) to a RNAse-free test tube to which DEPC-dH$_2$O was added to the final volume of 20 μl. The whole mixture was thoroughly stirred and then reacted at 37° C. for one hour [see, Molecular Cloning, Vol. II, 14, pp20–21]. Then, the mixture was heated at 95° C. for 5 minutes to terminate the reaction and treated with NaOH to obtain a single-stranded cDNA which is then used as a template for polymerase chain reaction(PCR).

1×Taq polymerase buffer (50 mM Tris-Cl, pH8.3, 3 mM MgCl$_2$, 250 μg/ml BSA), 200 μM of dNTP, 0.25 μM (10 pmol) of each of primers 5'-GGGAAATTGAGGGCTTTCGC-3' and 5'-CTGAAGCAATAGTTGGTGTC-3', 2 μg of cDNA as prepared above and 0.1 U of Taq polymerase were introduced into a 0.5 ml Eppendorf test tube and then sterilized dH$_2$O was added to make the reaction solution to the total volume of 10 μl, which was then thoroughly mixed. Then the test tube was centrifuged for a short time and the reaction solution attached to the wall of the test tube was collected on the bottom of the test tube. This reaction solution was carefully transferred to a glass-made capillary tube while keeping this tube to be free from foam and then both ends of capillary tube were melted and sealed under heating. Then, PCR amplification was carried out repeatedly 35 to 45 cycles using a thermal cycler(FTC-2000), with one cycle comprising 5 seconds at 95° C., 5 seconds at 55° C. and 15 seconds at 72° C. The amplified DNA was subjected to an electrophoresis using 1% Seakem agarose gel, stained with 50 μg/ml of ethidium bromide solution and then identified by using a UV transilluminator. As a result, it could be determined that in the tissue of mouse to which anti-sense oligodeoxynucleotide to TGF-β according to the present invention was administered the strength of ethidium bromide staining is much weaker than that in the tissue of the non-treated control group. From this result, it could be identified that anti-sense oligodeoxynucleotide to TGF-β can be bound to the front part of a structural gene for TGF-β to specifically inhibit the expression of TGF-β depending on the used dose. Accordingly, on the basis of such a dose-dependent inhibition the amount of anti-sense oligodeoxynucleotide capable of completely inhibiting TGF-β expression can be determined according to the number of cells present in wound portion and then utilized as an ideal dose thereof which can induce the clinically effective treatment effect on wound.

2) in situ Hybridization:

The desired TGF-β gene was inserted into the corresponding EcoRI-cutting site of plasmid vector pBluescript (commercially available from Clontech) to prepare the recombinant plasmid which is then introduced into E. coli HB101 to obtain a transformant. The transformed E. coli HB101 thus obtained is incubated to produce the desired plasmid in large quantities which is then purified with cesium centrifuge. Thereafter, in vitro transcription with SP6 (or T3) T7 RNA polymerase was carried out at 37° C. for 1 to 2 hours using a RNA labelling kit (made by B.M. Co., Ltd.). After the transcription reaction is completed, the template DNA was cleaved with DNase I and precipitated with ethanol to recover the RNA probe as a residual product. The recovered RNA probe was dissolved in 50 μl of 10 mM DTT, 10 mM Tris-HCl, 1 mM EDTA (pH7.6) and then used in hybridization. Upon the reaction is completed, the same amount of neutralizing buffer (300 mM CH$_3$COONa, pH6.0, 1% CH$_3$COOH, 10 mM DTT) was added to the reaction mixture and then ethanol was added to precipitate the desired probe.

0.5 μg of the probe as obtained above was mixed with 100 μl of a hybridization reaction solution (consisting of 50% deionized formamide, 10 mM Tris-HCl, pH7.6, 200 μg/ml of RNase-free tRNA, 1×Denhardt solution, 10% dextran sulphate, 600 mM NaCl, 0.25% SDS) and then 50 to 100 μl of the mixture was loaded on each slide glass to which mouse wound tissue as prepared above 1) was attached, and was subjected to hybridization for 16 to 22 hours while covering the slide glass with cover glass. After the hybridization is completed, the cover glass was removed from the slide glass in 5× SSC at 50° C., and the hybridized product was treated with RNase to remove unnecessary signals.

For the hybridized product, the coloring reaction was induced by means of DIG ELISA DNA labelling and detection kit (B.M. CO., Ltd.). Specifically, the hybridized product was placed in 100 mM Tris-HCl, pH7.5, 150 mM NaCl (TS) for about 5 minutes, removed, placed again in a blocking solution wherein dry milk powder free from fat and sugar is dissolved in TS in the concentration of 1.5%, and then allowed to stand for 30 minutes at room temperature. Thereafter, 0.2 units of alkaline phosphatase-conjugated anti-digoxigenin antibody diluted in 500 to 1000 times volume of TS was added and the mixture was reacted for 30 to 60 minutes. After the reaction is completed, the product was washed twice with TS for 15 minutes each time and then briefly washed in 100 mM Tris-HCl, pH9.5, 100 mM NaCl, 500 mM MgCl$_2$(TSM). The product was then stained with nitroblue tetrazolium (NBT) diluted in TMS and 5-bromo-4-chloro-3-indolyl phosphate (BCIP) solution for one to two days. Then, TE buffer (Tris-HCl 10 mmol/L, EDTA 1 mmol/L, pH8.0) was added to terminate the coloring reaction and the slide glass was mounted with aqueous crystal mount. The result was determined from the staining condition.

As a result thereof, in the control group not treated with anti-sense oligodeoxynucleotide mRNA for cytokines was slightly detected on the first day from wound development but could be detected mainly in macrophage on and after the third day. On the other hand, in the test group treated with anti-sense oligodeoxynucleotide SEQ ID NO:1 the signal for mRNA of TGF-β was not detected. According to this, it can be clearly seen that the expression of cytokine TGF-β can be inhibited by anti-sense oligodeoxynucleotide.

EXAMPLE 4

For the anti-sense oligodeoxynucleotide according to the present invention, the scarring inhibition activity was determined in the following manner.

Wound was artificially induced on the back of 40 rats in diameter of about 6 mm and the rats were divided into two groups, each of which consists of 20 rats. In the first group, the wound portion was treated by spraying 50 μM of anti-sense oligodeoxynucleotide 5'-CCGAGAGCGCGAACAGGGC-3' (SEQ ID NO:1) to TGF-β as prepared according to Example 1 (the anti-sense treated group). In the remaining one group, the wound was not treated with anti-sense oligodeoxynucleotide (the non-treated control group). Thereafter, the collagen content and tensile strength of the wound portion as important parameter for scarring were determined as time goes by. From this result, the scarring inhibition activity of anti-sense oligodeoxynucleotide according to the present invention could be identified. The results were represented in the following Tables 1 and 2.

TABLE 1

Collagen content in wound portion (μg/mg of tissue)

| Time elapsed | Collagen content | |
|---|---|---|
| | Non-treated control group | Anti-sense treated group |
| 1 day | 125 | 70 |
| 3 days | 159 | 82 |
| 7 days | 208 | 96 |
| 14 days | 261 | 254 |
| 50 days | 405 | 350 |

TABLE 2

Tensile strength of wound portion (MPa)

| Time elapsed | Tensile strength | |
|---|---|---|
| | Non-treated control group | Anti-sense treated group |
| 1 day | — | — |
| 3 days | 0.12 | 0.20 |
| 7 days | 0.65 | 0.87 |
| 14 days | 0.87 | 0.94 |
| 50 days | 11.53 | 13.06 |

As can be seen from the results shown in Tables 1 and 2, in rats treated with anti-sense oligodeoxynucleotide to TGF-β according to the present invention the collagen content was significantly lower than that in the non-treated control group but the tensile strength was rather higher in spite of such low collagen content. In addition, the administration of anti-sense oligodeoxynucleotide according to the present invention does not cause the delay of wound healing and can treat the wound so that it appears more nearly to be the normal tissue in comparison with that in the control group. Thus, it can be seen that the anti-sense oligodeoxynucleotide according to the present invention provides a superior tissue regeneration property whereby the wound can be substantially perfectly treated to the extent that the wound portion could not be visibly distinguished from the normal tissue.

Such results thus obtained can be assumed to be originated from the effect of anti-sense oligodeoxynucleotide to TGF-β of inhibiting the expression of TGF-β occurring generally in the wound portion and of inhibiting the division of fibrous cells and the overproduction of connective tissue caused by growth factor. In addition, the administration of such anti-sense oligodeoxynucleotide as soon as possible, particularly immediately after the wound occurs, is preferable for the increase of its effect and can lower the vascularization.

EXAMPLE 5

To identify the inhibitory activity of anti-sense oligodeoxynucleotide to TGF-β mRNA against TGF-β production, the following in vitro experiment was performed using nine kinds of S thiolated anti-sense oligodeoxynucleotide prepared in Example 2 and non-sense oligomer in A549 human lung carcinoma cell line and CCL-64 (mink lung epithelial cell). In this experiment, first the production of TGF-β from A549 cells stimulated by cyclosporin [see, Khanna, A., B. Li, K. H. Stenzel and M. Suthanthiran, 1994, Regulation of new DNA synthesis in mammalian cells by cyclosporin, Transplantation 57: 577–582] was inhibited by treatment with anti-sense oligodeoxynucleotide for TGF-β mRNA and then CCL-64 cells which are very sensitive to TGF-β and of which proliferation is significantly inhibited by TGF-β, were grown in the same medium to practice the bioassay which determines the quantity of TGF-β secreted in the medium [see, Danielpour, D., L. L. Dart, K. C. Flanders, A. B. Roberts and M. B. Sporn, 1989, Immunodetection and quantitation of the two forms of transforming growth factor-beta (TGF-β1 and TGF-β2) secreted by cells in cultures, J. Cell Physiol. 138: 79–86].

Specifically, at the first stage A549 cells were grown in OPTI-MEM medium containing 5% fetal bovine serum to the cell number of 10,000/ml. Then, the cells were distributed in a 24-well plate, incubated for 24 hours at 37° C. and then washed with a medium containing 0.1% fetal bovine serum. 1 ml of the same 0.1% FBS medium was distributed in each well which was treated with each of nine S thiolated anti-sense oligomers to TGF-β (SEQ ID NOS: 2–10) and non-sense oligomer (5'-AAATTTGGGCCCAAA-3' (SEQ ID NO:13) in the final concentration of 10 μM and then treated with 1 μg/ml of cyclosporin. The cells are incubated at 37° C. for additional 24 hours. After 24 hours, the medium were collected to use as the bioassay sample in the following procedure.

Bioassay procedure was conducted in the following manner: CCL-64 mink lung epithelial cells were grown in MEM medium containing 10% fetal bovine serum(FBS). When the cell number reaches 20,000 cells/100 μl, the cells were distributed in 96-well plate in an amount of 100 μl per each well and incubated for 24 hours at 37° C. in a suitable incubator. After 24 hours, the cells were washed with assay buffer [MEM supplemented with 0.2% FBS, 10 mM HEPES, pH 7.4, penicillin (25 units/ml) and streptomycin (25 μg/ml)] and then adjusted to 90 μl with the same assay buffer. 10 μl of each of the standard TGF-β solution having known concentration and the bioassay sample as obtained from A549 cell incubation above was added to each well of the plate. After 24 hours, the number of living cells was counted to determine the quantity of TGF-β secreted in the medium. The measured result is described in the following Table 3.

TABLE 3

The effect of all-thiolated anti-sense oligonucleotide (15mer) to the TGF-β mRNA on the inhibition of TGF-β secretion

| S thiolated 15mer anti-sense oligomer | TGF-β secreted in medium (ng/ml) |
|---|---|
| 1. 5'-GGTGTGGTGGGGAGG-3'(SEQ ID NO:2) | 2.3 |
| 2. 5'-GGCTGGGGGTCACCC-3'(SEQ ID NO:3) | 3.8 |
| 3. 5'-AGAGAGATCCGTCTC-3'(SEQ ID NO:4) | 1.9 |
| 4. 5'-CCCGGAGGGCGGCAT-3'(SEQ ID NO:5) | 1.2 |
| 5. 5'-GGCAAAAGGTAGGAG-3'(SEQ ID NO:6) | 2.1 |
| 6. 5'-GAAAGCTGAGGCTCC-3'(SEQ ID NO:7) | 3.6 |
| 7. 5'-GAGAAGGGCGCAGTG-3'(SEQ ID NO:8) | 1.5 |
| 8. 5'-GTGGAGGGGAGGCTT-3'(SEQ ID NO:9) | 2.7 |
| 9. 5'-TGTCTCAGTATCCCA-3'(SEQ ID NO:10) | 3.3 |
| 10. non-sense oligomer 5'-AAATTTGGGCCCAAA-3'(SEQ ID NO:13) | 5.0 |
| 11. Control | 5.1 |

As the result of the above experiment, it could be identified that all of nine S-thiolated anti-sense oligomers SEQ ID NOS. 2 to 10 according to the present invention very highly inhibit the TGF-β production in comparison with the non-sense oligomer used as the negative control. Particularly, among the above anti-sense oligodeoxynucleotides to TGF-β SEQ ID NO:5 and SEQ ID NO:8 shows an excellent inhibitory activity against TGF-β production.

EXAMPLE 6

On the basis of the result of the above Example 5, two anti-sense oligomers showing excellent inhibitory activity against TGF-β production, i.e. SEQ ID NOS:5 and 8 (S thiolated form), another one oligomer SEQ ID NO: 3 (S thiolated form) showing somewhat less inhibitory activity against TGF-β production and the non-sense oligomer (5'-AAATTTGGGCCCAAA-3' (SEQ ID NO:13) were selected to identify their scarring inhibition activities.

After 10 rats were anesthesized with ether, the hair on the back portion of rat was completely removed by using a hair cutter and then the back portion from the center to the limbs was cut down with a size having 1 cm length on four positions at the same intervals up to just above the muscle. The artificially wounded portions were then treated with the above mentioned four kinds of anti-sense or non-sense oligomers for the first 3 days at the concentration of 50 μM. The scarring inhibitory effect was observed during 3 weeks after treatment. The result can be shown in FIG. 2.

Figure 2:
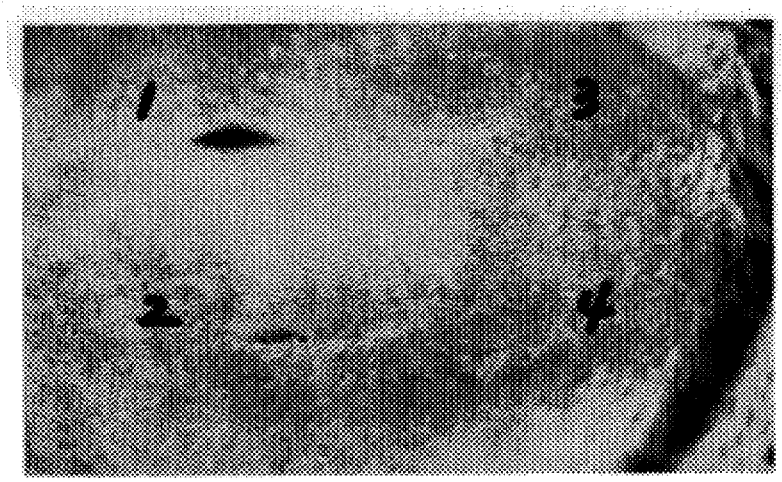
FIG. 2 is a photograph showing wound-healing effects of anti-sense oligodeoxynucleotides to TGF-β in rat [1: wound treated with non-sense oligomer, 2: wound treated with SEQ ID NO:3: wound treated with SEQ ID NO:5, 4: wound treated with SEQ ID NO:8]

As can be seen from FIG. 2, the scar formation was inhibited in the similar manner as in the above in vitro experiment. That is, it could be identified that anti-sense oligodeoxynucleotides of SEQ ID NOS:5 and 8 show a superior inhibitory activity against scar formation.

EXAMPLE 7

To identify whether the inhibition of scar formation is due to the decrease of TGF-β mRNA production by the anti-sense oligomer, the following Northern blot test was conducted.

First, from surgically wounded rats used in Example 6 above the wounded tissues were taken after 24 hours from the anti-sense oligomer treatment as the sample for Northern blot test. Total RNA was separated from the tissue by the LiCl-urea method and then subjected to electrophoresis using 1.2% agarose-formaldehyde gel. The gel was transferred to nylon membrane by means of capillary action in 20× SSC (1× SSC=0.15M NaCl, 0.015M sodium citrate, pH 7.2). After the membranes are subjected to prehybridization, the membranes were hybridized with [α-$^{32}$P] dCTP labelled probes in 50% formamide, 4× SSC, 1×X Denhardt's solution and 10 mg/ml salmon sperm DNA for 16 hours at 42° C. Then the nylon membranes were washed, dried and examined by autoradiography. The result can be shown in FIG. 3.

Figure 3:
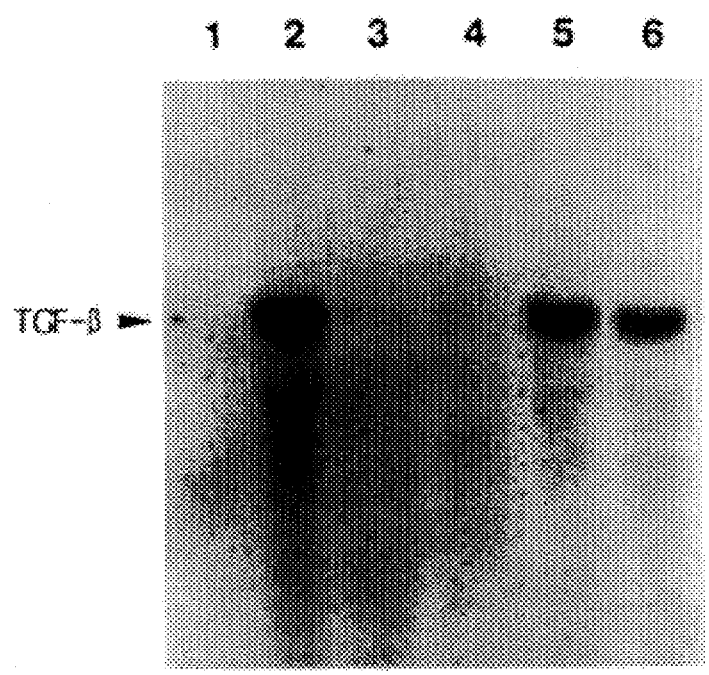
FIG. 3 is a photograph showing the inhibitory effect of anti-sense oligodeoxynucleotide to TGF-β against TGF-β mRNA production in wound site of rat, as measured by Northern blotting test [Lane 1: normal skin, Lane 2: wounded skin after 1 day, Lane 3: wound skin treated with SEQ ID NO:5, Lane 4: wounded skin treated with SEQ ID NO:8, Lane 5: wounded skin treated with non-sense oligomer, Lane 6: wounded skin treated with SEQ ID NO:3].

As can be seen from FIG. 3, TGF-β mRNA was significantly increased (lane 2) after wounding and then almost completely inhibited by treatment with anti-sense oligodeoxynucleotides of SEQ ID NOS:5 and 8 (lanes 3 and 4).

As can be noted from the above, since the anti-sense oligodeoxynucleotide to fibrogenic cytokine TGF-β according to the present invention inhibits the genetic expression of cytokine TGF-β which is secreted in large quantities in the wound portion to stimulate the scarring, it can be utilized as a medicinal agent useful for inhibiting the scarring in wound portion to treat the wound to the extent that the wound portion cannot be visibly distinguished from the normal tissue.

The more pertinent important features of the present invention have been outlined above in order that the detailed description of the invention which follows will be better understood and that the present contribution to the art can be fully appreciated. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

What is claimed is:

1. An anti-sense oligodeoxynucleotide, in that can be complementarily bound to mRNA of TGF-β to inhibit the genetic expression of TGF-β and is selected from the group consisting of:

5'-CCGAGAGCGCGAACAGGGC-3' (SEQ ID NO:1);
    5'-GGTGTGGTGGGGAGG-3' (SEQ ID NO:2);
    5'-GGCTGGGGGTCACCC-3' (SEQ ID NO:3);
    5'-AGAGAGATCCGTCTC-3' (SEQ ID NO:4);
    5'-CCCGGAGGGCGGCAT-3' (seq ID NO:5);
    5'-GGCAAAAGGTAGGAG-3' (SEQ ID NO:6);
    5'-GAAAGCTGAGGCTCC-3' (SEQ ID NO:7);
    5'-GAGAAGGGCGCAGTG-3' (SEQ ID NO:8);
    5'-GTGGAGGGGAGGCTT-3' (SEQ ID NO:9); and
    5'-TGTCTCAGTATCCCA-3' (SEQ ID NO:10).

2. The anti-sense oligodeoxynucleotide as defined in claim 1, wherein said anti-sense oligodeoxynucleotide is modified by substitution of oxygen atom in phosphate group of each base with sulfur atom to produce a S thiolated form thereof.

3. The anti-sense oligodeoxynucleotide as defined in claim 1, wherein said anti-sense oligodeoxynucleotide is 5'-CCCGGAGGGCGGCAT-3' (SEQ ID NO:5) or 5'-GAGAAGGGCGCAGTG-3' (SEQ ID NO:8) or S thiolated form thereof.

4. A scarring inhibiting composition which comprises at least one anti-sense oligodeoxynucleotide to mRNA for TGF-α as defined in claim 1.

5. The scarring inhibiting composition as defined in claim 4, wherein it contains anti-sense oligodeoxynucleotide 5'-CCCGGAGGGCGGCAT-3' (SEQ ID NO:5) or 5'-GAGAAGGGCGCAGTG-3' (SEQ ID NO:8) or S thiolated form thereof.

6. The scarring inhibiting composition as defined in claim 4, further comprising a pharmaceutically acceptable carrier, adjuvant or excipient.

7. The scarring inhibiting composition as defined in claim 4, wherein it is formulated in the form of an injection, a spray, an ointment or a cream.

8. A method of scar inhibition comprising administering on a wound lesion or peripheral tissue surrounding said wound lesion an effective amount to inhibit scar formation of at least one anti-sense oligodeoxynucleotide to TGF-β mRNA as defined in claim 1.

9. A process for producing anti-sense oligodeoxynucleotide to mRNA for TGF-β as defined in claim 1 comprising the steps of:

(a) synthesizing by means of an automatized DNA synthesizer, anti-sense oligodeoxynucleotide to mRNA for TGF-β;

(b) binding a linker sequence to each end of the synthesized anti-sense oligodeoxynucleotide sequence, of step (a) to form a combined sequence and then inserting the combined sequence into a suitable plasmid to obtain a recombinant plasmid;

(c) transforming suitable host bacteria with the recombinant plasmid obtained in step (b) to obtain a transformant; and (d) incubating the obtained transformant to express the desired anti-sense oligodeoxynucleotide in large quantities.

* * * * *